United States Patent [19]

Kantorski

[11] 4,220,038
[45] Sep. 2, 1980

[54] APPARATUS FOR MONITORING INSTRUMENT READINGS OF TRANSIENT FORCE OF A MOVING FLUID COLUMN

[75] Inventor: Joseph W. Kantorski, Southbridge, Mass.

[73] Assignee: American Optical Corporation, Southbridge, Mass.

[21] Appl. No.: 55,840

[22] Filed: Jul. 9, 1979

[51] Int. Cl.³ .................................... G01L 25/00
[52] U.S. Cl. ..................... 73/1 B; 73/4 R; 73/861.76
[58] Field of Search ................... 73/1 B, 4 R, 228

[56] References Cited

U.S. PATENT DOCUMENTS

| 2,316,255 | 4/1943 | Knobel et al. | 73/228 |
| 3,889,518 | 6/1975 | Denouter | 73/4 R |
| 4,000,640 | 1/1977 | Kocmich | 73/1 B |

Primary Examiner—S. Clement Swisher
Attorney, Agent, or Firm—Jeremiah J. Duggan; Alan H. Spencer; Stephen A. Schneeberger

[57] ABSTRACT

A device for verifying instrument readings of transient force of a moving fluid column including a paddle depending from a taut wire torsion bar. The unit is adaptable to instruments utilizing fluid pulses in testing objects for resistance or vulnerability to fluid stream pressure, e.g. ophthalmic tonometers. With disposition of the paddle in an instrument fluid path and a known torsional force applied to the supporting wire, the force required of a fluid column to displace the paddle may be established for verification of instrument readings and/or indication of defective instruments.

2 Claims, 5 Drawing Figures

APPARATUS FOR MONITORING INSTRUMENT READINGS OF TRANSIENT FORCE OF A MOVING FLUID COLUMN

BACKGROUND OF THE INVENTION

1. Field of the Invention:

This invention relates to fluid force measuring, testing and/or pressure verifying devices with particular reference to a highly sensitive system for verifying tonometer instrument readings of transient force of fluid pulses used to applanate the eye.

2. Discussion of the Prior Art:

Included among instruments which utilize fluid columns to determine internal pressure of resilient bodies is a tonometer which uses a fluid pulse to applanate the eye. U.S. Pat. Nos. 3,585,849; 3,572,100 and 3,538,754 are exemplary. While the sensitivity of such an instrument to intraocular pressures is of extreme importance, accuracy of reporting usually by direct reading display is equally critical. Reliable verification of instrument readings, calibration and/or indication of defective instruments is required.

Ocular simulators formed of variously shaped flexible materials have met with only limited success due to their relatively inconsistent response to instrument fluid pulses. Stresses and strain transfer from supporting structures and environmental conditions are considered probable causes.

While greater consistency in instrument reading verification may be realized by the use of an artificial rubber eye as a test object, e.g. as disclosed in U.S. Pat. No. 3,889,518, there are attending problems. For example, to simulate various degrees of intraocular pressures several test eyes of differing degrees of stiffness are required. Also, in the casting of artificial eyes of the usual inorganic compounds, ultimate stiffness cannot be predicted and variations in stiffness occur from day to day as a result of repeated use (material fatigue), changes in environmental conditions and/or turbulence within the diameter of the fluid column. Furthermore, in order to obtain a calibration value for a test eye, the fluid force necessary to cause applanation must be known beforehand.

In view of the foregoing, it is an object of this invention to provide for verification or calibration of air-pulse tonometer and other instrument readings and/or discovery of instrument malfunction by direct monitoring of force of emitted fluid.

Another object is to verify readings of transient force of a moving fluid column in tonometers and other such instruments by mechanical means and without reliance upon relatively unstable prior art artificial eyes and/or other flexible membranes.

Still another object is to provide an instrument calibrating and/or testing system utilizing sound mechanical principles and materials offering long useful life.

In connection with the foregoing, it is a further object to accomplish long useful life of instrument calibrating and/or testing means with use of materials and mechanical design which minimizes, if not eliminates, wear with use and are not subject to changes in environmental conditions.

Other objects and advantages of the invention will become more readily apparent from the following description.

SUMMARY OF THE INVENTION

The foregoing objects and corollaries are accomplished by positioning in the path of a moving fluid column to be monitored, a paddle with a lever arm depending from a taut torsion wire. The force required to swing the paddle from one given position to another in the fluid column path is adjustable by regulation of torque applied to the wire.

In a preferred embodiment of the invention, the paddle is initially held in a slightly angularly displaced relationship with the axis of the fluid column path and provided with known or no torque applied to the taut wire whereby the fluid force required to swing the paddle into an orthogonal relationship with the fluid column path can be straightforwardly mathematically determined.

With detection of the paddle reaching and/or passing through orthogonality with the fluid path and knowledge of torque developed in the paddle supporting wire at paddle orthogonality (i.e. from a zero starting torque or a known starting torque added to the finally developed torque) an accurate measure of the fluid force can be determined and/or verification of instrument readings made, i.e. detection of inaccuracies of instrument readings and/or determination of extent of instrument adjustment needed may be made.

Various settings of starting torque in the paddle supporting wire provide for the monitoring of low, medium or high fluid column forces with the present single apparatus. The expression "monitoring" where used herein is to be interpreted in its broadest sense, i.e. as including testing, checking, regulating, verifying or measuring.

Details of the invention will be more readily understood by reference to the following description when taken in conjunction with the accompanying drawings.

IN THE DRAWINGS

DESCRIPTION OF THE PREFERRED EMBODIMENTS

Figure 1:
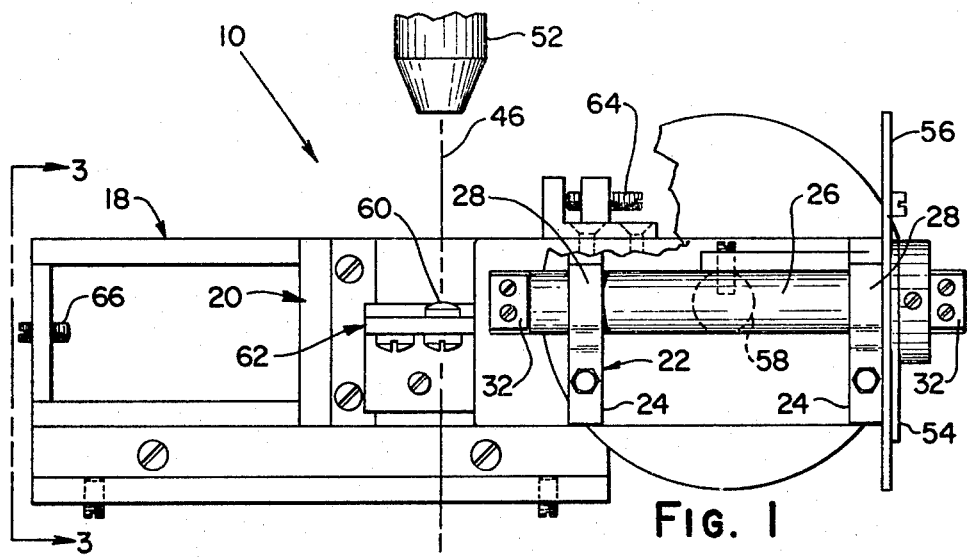
FIG. 1 is a plan view of an embodiment of the present invention.

Referring to the drawings, apparatus 10 comprises a main supporting body 12 (FIG. 2) having means for attachment to an instrument (e.g. an air-pulse tonometer) to be tested and/or calibrated. To this end, main body 12 is afforded an apertured collar 14 at each of its ends, only one of which is illustrated. Collars 14 are adapted to fit about typical tonometer browrest uprights such as are illustrated in U.S. Pat. No. 3,889,518, for example. A set screw 16 in each collar is used to lock supporting body 12 in a desired adjusted position on the tonometer instrument. It should be understood that the illustrated collar 14 and set screw may alternatively comprise any other suitable form of clamping means such as C-clamps or specially designed sliding locks.

Figure 2:
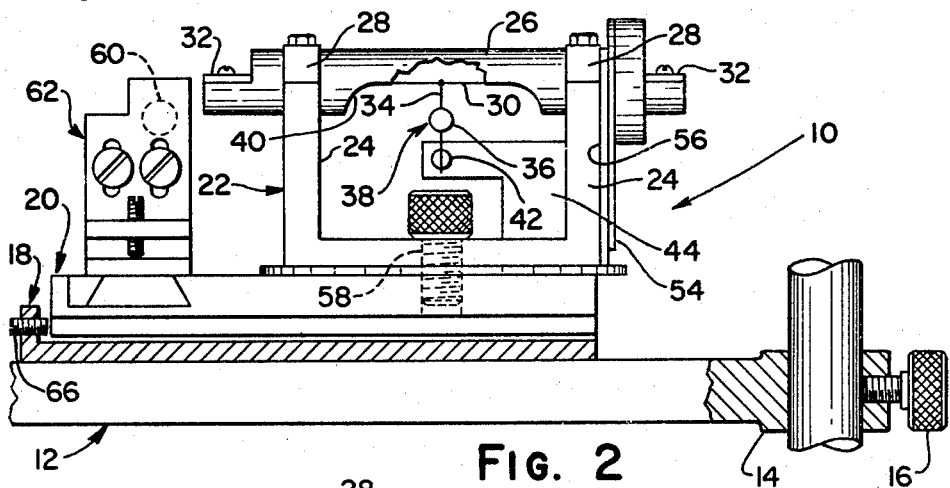
FIG. 2 is a partially cross-sectioned elevational view of the apparatus.
Figure 3:
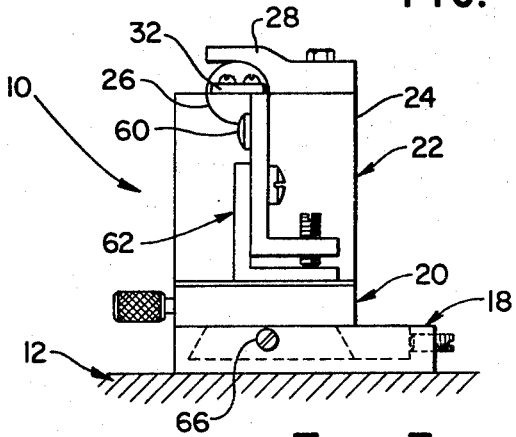
FIG. 3 is a view of one end of the apparatus taken from line 3—3 of FIG. 1.
Figure 5:
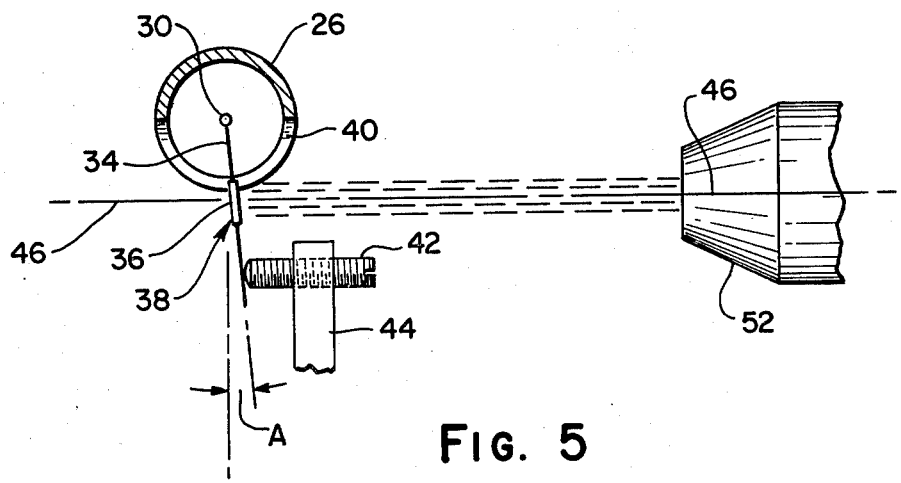
FIG. 5 is a partially cross-sectioned diagrammatic illustration of the function of principal components of the apparatus.

Fixed to main body 12 is slideway 18 carrying slide 20 upon which is mounted fluid column monitoring means which includes the following:

Swivel mounted on slide 20 is bracket 22 having spaced uprights 24 in which opposite ends of tube 26 are socketed for rotational adjustment when needed and selective locking in place by clamps 28. Extending longitudinally, approximately centrally through the hollow interior of tube 26, is torsion wire 30 (FIGS. 2 and 5). Wire 30 is held taut in tube 26 with clamping plates 32.

Intermediately of the extension of wire 30 between uprights 24 is depending lever arm 34 (FIGS. 2 and 5) preferably also formed of wire and soldered, brazed or otherwise fixed to wire 30. Lever arm 34 supports disc 36 and the combined arm 34 and disc 36 which will be referred to hereinafter as paddle 38. Cutout 40 in tube 26 affords clear space for swinging paddle 38 about the axis of carrier wire 30 as will be described in detail shortly.

Adjacent lever arm 34 is adjustable stop 42 which is supported by an extension 44 of bracket 22. Following longitudinal adjustment (e.g. by threading) and fixing of stop 42 in extension 44, counterclockwise rotation of tube 26 as viewed in FIG. 5, affords tilting of paddle 38 relative to the axis 46 of a path of fluid 48 (FIG. 5) to be monitored. This counterclockwise rotation of tube 26 to the extent of causing arm 34 to just reach stop 42 affords substantially no torque in the paddle carrying wire 30 but, forcing paddle 38 to return to a vertical dependency from tube 36 by incidence of a stream or pulse 50 of fluid (e.g. air) induces a readily mathematically determinable torque in wire 30 upon arrival of paddle 38 at the aforesaid vertical dependency. Thus, the force of stream or pulse 50 becomes known for verification of the tonometer instrument reading of force emitted from nozzle 52.

Those desiring greater details of operation and function of air pulse tonometer mechanisms and their respective pressure reading systems may refer to the aforementioned U.S. Pat. No. 3,889,518 and/or references cited therein.

In instances of need to monitor greater than the above discussed minimum air pulse pressure, counterclockwise rotation of tube 26 (FIG. 5) continued after bringing arm 34 into contact with stop 44 applies a torque to wire 30 which increases the force needed to return paddle 38 to the aforesaid vertical dependency. Adjustment of stop 42 in extension 44 regulates the angular travel A (FIG. 5) required of paddle 38 to reach a vertical dependency from tube 26.

Figure 4:
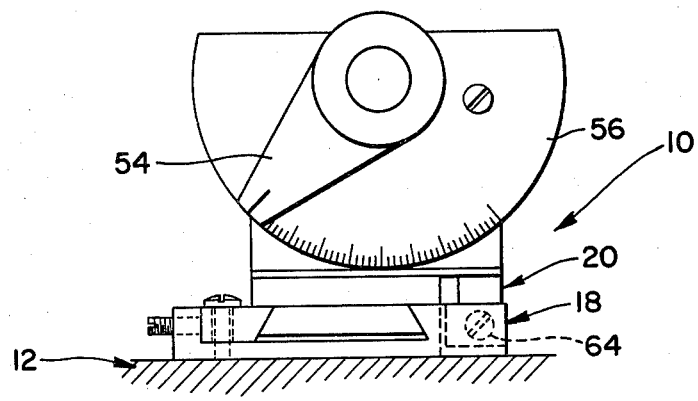
FIG. 4 is a view of the opposite end of the apparatus.

Rotational adjustment of tube 26 is facilitated by provision of lever 54 (FIGS. 1, 2 and 4) which is clamped to tube 26 and backed by stationary protractor 56. Indicia on protractor 56 may be so graduated as to indicate angular adjustment of lever arm 34 directly or to read in increments of torque applied to wire 30 and/or units of force required to move paddle 38 to verticality.

Since accurate centering of disc 36 of paddle 38 upon axis 46 is critical to precision in tonometer instrument reading verification, the following alignment means and procedure are provided:

Vertical adjustment of disc 36 relative to axis 46 may be accomplished by movement of main body 12 as needed along the aforesaid headrest supports of the tonometer instrument.

Rotational adjustment or pivoting of disc 36 may be accomplished by rotating bracket 22 on slide 20 about swivel post 58 which also functions as a clamp screw.

Horizontal alignment of disc 36, together with the aforesaid vertical alignment, may be accomplished with simulated ocular cornea 60 which also provides for setting of the distance between disc 36 and nozzle 52 of the tonometer instrument, i.e. by movement of nozzle 52 toward and away from cornea 60.

Artificial cornea 60 is carried by support 62 on slide 20 the former being independently vertically adjustable for initial establishment of leveling of center of the artificial cornea with center of disc 36.

Adjustable stop 64 (FIG. 1) fixed to slideway 18 locates artificial cornea 60 at a given position relative to main body 12 whereupon manipulation of nozzle 52 with the usual tonometer joy stick allows centering of its axis 46 with the center of artificial cornea 60. The usual tonometer instrument sighting through nozzle 52 permits the above alignment procedure.

Thereafter, movement of slide 20 away from stop 64, (e.g. to the left as viewed in FIG. 1) and against stop 66 brings disc 36 of paddle 38 into exact correspondence with the previous position of artificial cornea 60.

Emission of fluid from nozzle 52 may now be monitored by the reaction of paddle 38 for verification and/or calibration of the tonometer instrument reading. Upon completion of instrument calibration, apparatus 10 is removed from the tonometer.

It should be appreciated that there are many modifications and adaptations of the precise form of the invention here shown which may suit particular requirements such as, for example, the monitoring of transient force of columns of fluid originating from sources other than air-pulse tonometers. Accordingly, the precise forms of the invention here shown and described are not to be interpreted as restrictive of the invention beyond that necessitated by the following claims.

I claim:

1. Apparatus for monitoring transient force of a moving fluid column comprising:
    a paddle having a lever arm and disc carried by said arm;
    paddle carrying means from which said lever arm depends, said carrying means resisting relative swinging movement of said paddle;
    means for supporting both said paddle and carrying means with said paddle in a position within a path along which a moving fluid column is to be monitored;
    means for aligning said disc of said paddle centrally in said path of said moving fluid column, said aligning means including a simulated ocular cornea fixed at a known position on said paddle supporting means relative to said paddle disc; and
    means for selectively adjusting the resistance of said carrying means to said relative swinging movement of said paddle.

2. Apparatus according to claim 1 wherein said supporting means for said paddle and carrier means includes a slide and slideway, there being a pair of fixed stops on said slideway for selectively locating said slide first at a position allowing alignment of a fluid column path to be monitored with said simulated cornea and secondly locating said slide at a position where said disc of said paddle is in correspondence with initial positioning of said simulated cornea whereby said disc becomes aligned with said fluid path.

* * * * *